United States Patent
Slater et al.

(10) Patent No.: US 7,183,064 B1
(45) Date of Patent: Feb. 27, 2007

(54) METHOD FOR IDENTIFYING PRE-NEOPLASTIC AND/OR NEOPLASTIC STATES IN MAMMALS

(75) Inventors: Michael Slater, Belmore (AU); Julian Barden, Marsfield (AU)

(73) Assignee: Biosceptre Pty Ltd, Sydney (AU)

( * ) Notice: Subject to any disclaimer, the term of this patent is extended or adjusted under 35 U.S.C. 154(b) by 0 days.

(21) Appl. No.: 10/019,356

(22) PCT Filed: Apr. 26, 2000

(86) PCT No.: PCT/AU00/00363

§ 371 (c)(1),
(2), (4) Date: May 21, 2002

(87) PCT Pub. No.: WO01/06259

PCT Pub. Date: Jan. 25, 2001

(30) Foreign Application Priority Data

Apr. 21, 1999 (AU) .................................. PP9911

(51) Int. Cl.
*G01N 33/574* (2006.01)
*G01N 33/48* (2006.01)
*G01N 33/566* (2006.01)

(52) U.S. Cl. .............. 435/7.23; 436/64; 436/501
(58) Field of Classification Search ............. 435/7.1, 435/7.23; 436/64, 63, 501
See application file for complete search history.

(56) References Cited

FOREIGN PATENT DOCUMENTS

| WO | WO9216558 | * 10/1992 |
|----|-----------|-----------|
| WO | WO 95/33048 | 12/1995 |
| WO | WO9706256 | * 2/1997 |
| WO | WO 97/41222 | 11/1997 |
| WO | WO 98/42835 | 10/1998 |

OTHER PUBLICATIONS

Jacob et al, Indian J Cancer. Jun. 2002; 39(2):61-5.*
Mauro et al, Curr Opin Oncol. Jan. 2001; 13(1):3-7.*
Meeker et al, Blood. 1989, vol. 74, pp. 1801-1806.*
Jameison et al (Journal of Cellular Physiology, 1996, vol. 166, pp. 637-642).*
Buell et al (Blood, 1998, vol. 92, pp. 3521-3528).*
Paul (Fundamental Immunology, Text, 1998, p. 107).*
Hopfner et al. (1998). *Biochem and Biophys Res Comm 251*: 811-817.
Nawa et al. (1999). *British J. of Cancer 80*: 1185-1189.
Urano et al. (1997). *Cancer Research 57*: 3281-3287.
Wurl et al. (1998). *Oncogene 16*: 1183-1185.
Di Virgilio, et al., *Drug Dev. Res.*, 45:207-213 (1998).
Gröschel-Stewart, et al., *Cell Tissue Res.*, 296:599-605 (1999).
Hansen, et al., *J. Neurol.*, 27:529-539 (1998).
Vulchanova, et al., *Neuropharmacol.*, 36(9):1229-1242 (1997).
Supplementary European Search Report, mailing date Dec. 9, 2002.

* cited by examiner

*Primary Examiner*—Karen A. Canella
(74) *Attorney, Agent, or Firm*—Ivor R. Elrifi; Naomi S. Biswas, Esq.; Mintz Levin

(57) ABSTRACT

The present invention relates to methods of identifying pre-neoplastic and/or neoplastic states in mammals and in particular to a method for identifying pre-neoplastic and neoplastic cells in tissues and body fluids, based on differential expression of purinergic receptors in these cells.

4 Claims, 9 Drawing Sheets

The following figure shows an example of the level of P2X1 labeling in a biopsy sample taken from a normal human prostate (left) and from a patient with advanced prostate cancer (right).

The following Figure shows that, compared with prostate epithelium (E) from a young (12 week) rat (left), tissue from an aged rat (18 months) shows marked hyperplasia (right).

The following figure shows an example of P2X1 labelling in normal breast (right) and a substantial down-regulation in breast tumour tissue (left).

(a) Low Power: normal tissue, P2X2 label. Bars = 50μm.

(b) Low Power: breast cancer, P2x2.

(c) Low Power: normal tissue, H&E stain. Bars = 50μm.

(d) Low Power: breast cancer, H&E stain.

(e) High Power: normal tissue, H&E stain.

(f) High Power: breast cancer, H&E stain.

(g) High Power: normal tissue, P2x2 label.

(h) High Power: cancer tissue, P2x2 label.

(j) High Power: cancer tissue, P2x3 label.

(l) High Power: cancer tissue, P2x7 label.

(i) High Power: normal tissue, P2x3 label. Bars 20 μm. Arrow = epithelial acinus.

(k) High Power: normal tissue, P2x7 label. Bars = 20μm. Arrows = epithelial acinus.

(m) Control: normal tissue, bar = 50 μm, erythrocytes with residual endogenase activity (arrow)

METHOD FOR IDENTIFYING PRE-NEOPLASTIC AND/OR NEOPLASTIC STATES IN MAMMALS

TECHNICAL FIELD

The present invention relates to methods of identifying pre-neoplastic and/or neoplastic states in mammals and in particular to a method for identifying pre-neoplastic and neoplastic cells in tissues and body fluids, based on differential expression of purinergic receptors in these cells.

BACKGROUND

When diagnosing cancer, cellular features in biopsy samples are taken into account such as, the degree of variability of cancer cell size and shape, the proportion of actively dividing cells and invasion into neighbouring structures. Commonly used histological stains are haematoxylin (primary stain) and eosin (counterstain) which differentially label subcellular elements. Other diagnostic methods employ antibodies to particular diagnostic molecules within (via intracellular epitopes) or on the surface of cells or tissues (via extracellular epitopes) which can be made visible for microscopic analysis eg, carcino-embryonic antigen (CEA). Some specific examples are discussed below.

Prostate Cancer

The incidence of prostate cancer in the Western world is increasing at an alarming rate, having more than doubled in the past five years. It has the highest incidence of any neoplasm, is second only to lung cancer as the most common cause of cancer death in men worldwide, and is the leading cause of death in Australia [1]. Benign prostatic hyperplasia (BPH) is common in men over 50 and is a possible precursor of prostatic intraepithelial neoplasia (PIN), itself a precursor to prostate cancer. Postmortem studies indicate that 70% of men have malignant cells in their prostate by the time they reach 80 [2]. This disease is characterised by a striking racial variation and is most prevalent in African-Americans, intermediate in Caucasians, slightly lower in Latinos, and least prevalent in Asians. In the latter group, it is nevertheless the most rapidly increasing form of neoplasm. Until recently, it was not clear if these differences were due to racial genetic variation or diet. Studies have now shown that diet is a primary influencing factor [3].

Current Diagnosis and Treatment of Prostate Cancer

Despite the gravity of this condition, diagnostic methods are few and imprecise. Current methods for assessing prognosis such as digital rectal examination (DRE), ultrasound, prostatic acid phosphatase levels, androgen ablation, prostate specific antigen (PSA) density, PSA velocity, PSA age-specific reference ranges and Gleason histopathological grading, can fail to provide reliable predictive information regarding the clinical outcome of prostate cancer [4]. For instance, studies have shown that DRE results in a 36.9% false negative rate [5]. PSA is a 33-kDa serine protease that is associated with a number of tissues besides prostate [6], is up-regulated by androgens, glucocorticoids and progestins and is thought to be involved in the regulation of growth factors. Unfortunately, serum PSA levels have an incidence of 23% false negative and 36.7% false positive diagnoses [6]. It has even been suggested that more than half of new screen-detected cases are in fact false positives [7]. Attempts to improve screening methods by the introduction of additional tests such as PSA density, velocity, and age-specific reference ranges has been equivocal. One study has shown that applying an age-specific PSA reference range that increases the upper limit of normal PSA to 4.5 ng/mL results in the failure to detect a substantial number of clinically significant cancers [8]. Given this uncertainty, prostate biopsy is often performed to confirm malignancy but this test also has a highly unsatisfactory 23% incidence of false-negative diagnosis [9].

Treatment selection is largely dependent on clinical staging based on microscopic analysis of tissue sections [10]. This technique depends on judgment and considerable experience in relating histological appearance to clinical outcome. Unfortunately, prostate cancer tissue is notoriously heterogeneous and a vital diagnostic feature may easily be missed in the section being examined. To further complicate the situation, there have been no randomised and controlled trials to examine the outcomes of surgery and radiotherapy [2]. Treatment choices include radical prostatectomy, radiation therapy, androgen deprivation and "watchful waiting". A definitive answer to the question of "watchful waiting" versus radical intervention awaits the conclusion of the prostate cancer intervention-versus-observation trial [11]. The consequences to the patient of these decisions are serious. Radical prostatectomy for instance, often results in incontinence, impotence, bladder neck stricture and depression [12]. Clearly, improved markers that reliably differentiate between benign prostatic hyperplasia (BPH), prostatic intraepithelial neoplasia (PIN), atypical adenomatous hyperplasia (AAH) and prostatic cancer are urgently needed.

The Role of P2X Receptors in Cancer

Neurotransmitters such as noradrenalin and acetylcholine act not only in the synapse and neuromuscular junction but also on transmitter-specific cell receptors in a wide variety of tissues and organs. These receptors are pore-like transmembrane channels that introduce ions into the cell. Adenosine triphosphate (ATP), best known as the molecular currency of intracellular energy stores, was first proposed as a peripheral neurotransmitter based on its ability to contract smooth muscle [13]. ATP acts in the same manner as other neurotransmitters and can activate both the (relatively slow) G protein-coupled tissue receptors (P2Y), the more recently characterised (fast) ligand-gated purinergic ($P2X_{1-7}$) ion channels and can also act as a co-transmitter. Despite its relatively recent discovery, it is likely that the purinergic transmitter system developed very early in evolution [14].

There are currently 7 genetically distinct P2X receptor subtypes. They are as widely distributed as receptors of the cholinergic and adrenergic systems and are found in most mammalian cells [14]. These receptors constitute a new class of fast-response, membrane-bound, ligand-gated, calcium-permeable, cation-selective channels that are activated by extracellular ATP from nerve terminals or a local tissue source [15–18]. They are predominantly permeable to calcium ions but also admit other cations, such as potassium and sodium, thereby mediating depolarisation [19]. For instance, in lung epithelia, P2X channels stimulate $Cl^-$ channel up-regulation, $K^+$ secretion and inhibit $Na^+$ absorption (21). ATP can stimulate both DNA synthesis and cell proliferation via the up-regulation of the P2X receptors [14]. This function is linked to stimulation of phospholipase C and ionic calcium release from inositol-phosphate-sensitive intracellular stores, as well as other signal transduction pathways. These actions are potentiated by the synergistic action of ATP with polypeptide growth factors [20]. The influx of calcium through the P2X receptors also triggers the secretion of other neurotransmitters, serves as a signal for the activation of calcium-dependent potassium channels, inactivates other calcium channel types, regulates endocytotic retrieval of synaptic vesicle membranes, enhances the synthesis of neurotransmitters, regulates pools of synaptic vesicles available for secretion and triggers several forms of synaptic plasticity. The variety of responses to a single stimulation of P2X receptors suggests there are many calcium-activated pathways [21].

Extracellular ATP, acting via the purinergic receptors, also has a direct anticancer effect on human breast cancer cells, prostate carcinoma cells, human adenocarcinoma cells and fibroblast cell lines. Cytotoxic T lymphocytes and natural killer (NK) cells release ATP when they attack tumour cells [22]. Only transformed cell growth is inhibited, by inducing S phase block, apoptosis, increased permeability to nucleotides, sugar phosphates, ions and synergy with other anticancer agents. None of these effects are noted on untransformed cells [14].

Curiously, tumour cells are known to contain exceptionally high levels of ATP [23]. Adenosine and ATP both increase intratumour blood flow by stimulating nitric oxide synthesis from the endothelium, thus inducing potent vasodilution [24]. In this case ATP acts through P2Y receptors (26). Nitric oxide release is also linked to P2X receptor function. For instance, 90% of the nitric oxide synthase activity found in non-pregnant sheep myometrium is calcium ion-channel dependent [25].

Epithelial adhesive proteins also play a major role in the spread of cancer [26]. In wound healing, cell injury signals propagate via extracellular P2X receptors and intercellular gap junctions, stimulating calcium ion-induced wave propagation [27]. Intracellular calcium ions admitted by the P2X channels trigger the transport of membrane-bound organelles along microtubules, remodelling of the ECM and up-regulation of the adhesion molecule E-cadherin [28]. The myoepithelial cells found in prostatic epithelial acinar exert important paracrine effects on carcinoma cells both in situ and in vitro. Cancer cells are also affected by high expression of ECM molecules, proteinase inhibitors and angiogenic inhibitor [29]. During metastatic invasion, extracellular calcium influx activates membrane-associated metalloproteinases that facilitate tissue penetration by invasive cells. Urokinase plasminogen activator has also been strongly implicated in the progression of several malignancies including breast and prostate cancer [30].

Current techniques for staging and diagnosing cancer need to be improved in order to provide more reliable results using relatively simple technology. It would also be advantageous to have a diagnostic method amenable to automation.

It is an object of the present invention to provide a method of identifying pre-neoplastic and/or neoplastic cells which will overcome or substantially ameliorate at least some of the deficiencies of the prior art or will provide a useful alternative.

SUMMARY OF THE INVENTION

The purinergic nervous system operates in parallel with the better known but slower acting adrenergic and cholinergic nervous systems. Like them, it operates in the brain, synapse, neuromuscular junction, peripheral nervous system and smooth muscle. The transmitter substance activating these fast-acting ligand-gated cation receptor channels is ATP, which acts by triggering purinergic receptors in tissues, resulting in a variety of metabolic responses including an influx of ions into the cell.

A unique suite of highly specific antibodies able to differentiate between the extracellular domains of each of the P2X purinergic receptor subtypes has been developed.

These receptors are readily visualised using immunocytochemical methods and present in a variety of expression patterns such as cell surface, tubular and punctate labelling. It has surprisingly been shown that the expression of P2X receptors is characteristic for pre-cancer and cancer stages and also for tissue from young vs old mammals. These changes are accompanied by marked differences in growth, extracellular matrix, metabolic and innervation factors as well as increases in subepithelial ionic calcium and microtubules. The invention therefore provides a new tool with which to diagnose pre-cancerous conditions, (such as hyperplasia), stage cancer and to investigate the basic physiology and aetiology of carcinogenesis.

According to a first aspect, the invention provides a method of staging and/or diagnosing pre-neoplastic and/or neoplastic states in a mammal, comprising detection of the P2X purinergic receptor expression profile of cells and/or tissue from said mammal and comparison of the profile with a predetermined expression profile of normal cells and/or tissue.

According to a second aspect, the invention provides a method of determining the aetiology of carcinogenesis in a mammal, comprising detection of the P2X purinergic receptor expression profile of cells and/or tissue from the mammal and comparison of the profile with a predetermined expression profile of normal cells and/or tissue.

According to a third aspect, the present invention provides a method of diagnosing prostate cancer in a subject, comprising detecting the expression profile of $P2X_1$, $P2X_2$, $P2X_3$, and/or $P2X_7$ purinergic receptors in prostate cells and/or tissue from the subject using $P2X_1$, $P2X_2$, P2X3 and/or $P2X_7$ antibody respectively, wherein an increase in the intensity of the P2X purinergic receptor expression profile in the prostate cells and/or tissue, compared to the expression profile of prostate cells and/or tissue from a prostate having benign prostate hyperplasia, is diagnostic of the presence of prostate cancer.

According to a fourth aspect, the present invention provides a method of diagnosing breast cancer in a subject comprising detecting the expression profile of $P2X_2$ or $P2X_3$, purinergic receptors in breast cells and/or tissue from the subject using $P2X_2$ or $P2X_3$, antibody respectively, wherein a decrease in the intensity of the P2X purinergic receptor expression profile in the breast cells and/or tissue from the breast of a normal subject, is diagnostic of the presence of breast cancer.

According to a fifth aspect, the invention provides use of P2X purinergic receptor antibody reagent to stage and/or diagnose a pre-neoplastic and/or neoplastic state in a mammalian subject.

According to a sixth aspect, the invention provides use of P2X purinergic receptor antibody reagent to determine the aetiology of carcinogenesis in a mammalian subject.

According to a seventh aspect, the invention provides an isolate mammalian cell or tissue sample complexed with a P2X purinergic receptor-specific antibody reagent.

According to an eight aspect, the invention provides a kit for diagnosing a pre-neoplastic and/or neoplastic state in a mammal comprising means for detecting P2X purinergic receptor expression profile in a sample comprising cells and/or tissue from the mammal and means for comparison of the expression level with a predetermined expression level.

According to a ninth aspect, the invention provides an antibody reagent specific for a P2X purinergic receptor, wherein the reagent is capable of differentiating between pre-neoplastic or neoplastic cells and/or tissue and normal cells and/or tissue.

According to a tenth aspect, the invention provides an antibody reagent specific for a P2X purinergic receptor when used to differentiate between pre-neoplastic or neoplastic cells and/or tissue and normal cells and/or tissue.

According to an eleventh aspect, the invention provides an antibody reagent specific for P2X purinergic receptor when used to differentiate between functional and non-functional P2X receptors in cells and/or tissue.

Preferably the mammal is a human although it will be clear to the skilled addressee that the method may be applied to any mammal. Preferably the cells are prostate tissue and/or cells or breast tissue and/or cells. The cells may be obtained by biopsy but may also be obtained from a body fluid or, in the case of prostate tissue and/or cells, from digital rectal examination exudate or from semen.

Preferably the antibody reagent comprises a polyclonal antiserum. Preferably the P2X antibody reagent is specific for $P2X_1$, $P2X_2$, $P2X_3$, $P2X_4$, $P2X_5$, $P2X_6$ or $P2X_7$ receptors, most preferably $P2X_1$, $P2X_2$, $P2X_3$ or $P2X_7$ receptors. It will be clear to those skilled in the art that the antibody reagent may be a suite of antibodies that may be polyclonal or monoclonal. It will also be clear to those skilled in the art that the suite of P2X receptor antibodies may comprise any combination of the P2X receptor subtypes, and in particular the combination of $P2X_1$, $P2X_2$, $P2X_3$ and $P2X_7$.

Preferably detection of P2X receptor expression profile is by immunohistochemical means. It will be clear to the skilled addressee that the P2X receptors may be detected by other means including ELISA, RIA or similar immunological techniques, depending on the source of the cell or tissue sample and the reagents available. Preferably, the P2X receptors are detected by a colorimetric assay. It will also be clear to those skilled in the art that Western blotting techniques and detection of P2X purinergic receptor mRNA may be useful in determining the P2X receptor expression profile.

In the context of the present invention, the term "pre-neoplastic cells" comprises cells that are hyperplastic or hypertrophic.

In the context of the present invention the term "suite of antibodies" comprises polyclonal antibodies which contain several different antibodies specific for the same or different antigens and which are able to specifically differentiate between each of the P2X receptor subtypes. When the antibodies are monoclonal, the term "suite of antibodies" also comprises a panel of antibodies able to specifically differentiate between each of the P2X receptor subtypes.

In the context of the present invention, detection of an "expression profile" comprises detection of a pattern or intensity of expression.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

BRIEF DESCRIPTION OF FIGURES

FIGS. 4a and 4d, H&E stain.

FIGS. 5a–c show core biopsies (supplied as 3 cores) from a 57-year old man with increasing PSA. Two cores were diagnosed as containing areas of BPH adjacent to areas of advanced cancer, Gleason score 8. FIG. 5a shows an area of BPH with no cancerous markers (5a-arrow) stained with H&E. FIG. 5b is a serial section from the same block labelled with $P2X_1$ antibody. The P2X labelling is characteristic of translocation Stage 2. The presence of these features, in tissue diagnosed by H&E staining as BPH, indicates not only the presence of preneoplastic change but that those changes are more advanced. FIG. 5e is a high-power micrograph from a serial section of the acinus arrowed in FIG. 5b. It depicts Stage 2 features as follows: some PEN remains (N-arrowhead) but most labelling is now punctate and cytoplasmic (P-arrow). Previous experiments have shown that each puncta is an individually-labelled P2X receptor or small localised patch of receptors. The lateral plasma membranes are clearly labelled (L-arrow) and there is labelling in the apical epithelium (A-arrow).

FIGS. 5d–f show a core biopsy (3 cores) from an 81-year old man with a PSA of 8.1. In this case the diagnosis was infiltrating adenocarcinoma, Gleason score 6. H&E staining (FIG. 5d) showed areas of both BPH and invasive cancer (prominent nucleoli, basement membrane invasion and abnormal acinal architecture). FIG. 5e shows an increase in P2X labelling in the apical epithelum (arrow) but a general decrease in overall signal. A high-power micrograph (FIG. 5f) shows these P2X labelling features to be typical of P2X translocation Stage 3. The labelling is less intense than that seen in Stage 2 (FIG. 5b), due to a concentration of label in the apical epithelium. The nuclei are devoid of label except for the nuclear membrane (N-arrow). The label is homogeneous rather than punctate, and is mostly found on the apical epithelium (A-arrow). At the completion of the translocation process, P2X label was commonly concentrated in the apical epithelium after which it was de-expressed (D). FIGS. 5a and 5d, H&E stain. FIGS. 5b, c, e and f, P2X immunoperoxidase label. No counterstain. Bar for low power micrographs (5a, b, d and e) is 1 cm=150 µm. Bar for high power micrographs (5c and f) is 1 cm=40 µm.

DESCRIPTION OF THE INVENTION

Figure 1:
FIG. 1 shows an example of the level of $P2X_1$ labelling in a biopsy sample taken from a normal human prostate (left) and from a patient with advanced prostate cancer (right).

A preferred embodiment of the invention will now be described by way of example only and with reference to the accompanying Figures.

EXAMPLE 1

Immunohistochemical Procedure

The immunohistochemical method used in this study was adapted from Barclay [31]. Sections with a thickness of 8 µm were cut from unfixed, frozen tissue using a Reichert Jung 2800 Frigocut cryotome. Sections were air dried at room temperature for 1 hour, fixed for 12 hours in acetone at −20° C. and air dried at room temperature for 1 hour prior to antibody labelling. They were then incubated at room temperature with one of either rabbit or sheep anti-$P2X_1$, $P2X_2$, $P2X_3$, $P2X_4$, $P2X_5$, $P2X_6$ or $P2X_7$ antibody. After washing, sections were then incubated in the secondary antibody; a 1:30 dilution of HRP-conjugated goat anti-rabbit secondary antibody (Dako) for 30 mins for rabbit primaries and HRP-conjugated goat anti-sheep secondary antibody (Dako) for sheep primaries. Slides were again rinsed and then immersed in 15% diaminobenzidine tetrahydrochloride (DAB—Sigma) for 10 minutes. Sections were rinsed, air dried and mounted in DPX (Merck). Control slides were incubated in diluent buffer during the first incubation and then treated in the same manner as the experimental slides. Negative control slides were treated in the same manner as the experimental slides except that the primary antibody was replaced with non-immune serum.

EXAMPLE 2

Antibody Production

The consensus sequences of the rat $P2X_1$ [32], $P2X_2$ [33], $P2X_3$ [34], rat $P2X_4$ [35], rat $P2X_4$ [36], rat $P2X_6$ [36], rat $P2X_7$ [37], human $P2X_7$ [38], human $P2X_1$ [39], human $P2X_3$ [40], human $P2X_4$ [41] and human $P2X_5$ [42] cloned receptors were examined for suitable epitopes following the approach adopted in Hansen et al. [15]. The non-homologous epitopes corresponding to the segment Lys199-Cys217 used in rat $P2X_1$ were utilised in rat $P2X_3$, rat $P2X_6$ and rat $P2X_7$. Variations were applied to rat $P2X_4$ which used the sequence Ile235-Gly251 to which was attached a C-terminal Cys residue for cross-linking to a 6 kDa diphtheria toxin domain. The $P2X_2$ epitope was selected from a region within the C1 domain [15], Cys130-Gly153. The rat $P2X_5$ epitope was selected from a region closer to the second transmembrane domain but still extracellular (Lys314-Ile333 to which was added a C-terminal Cys also for conjugation). Although largely homologous with rat $P2X_4$, cross-labelling of $P2X_4$ and $P2X_5$ did not occur. All antibodies against rat sequences were able to label corresponding human receptors. A separate epitope was used for the human $P2X_1$ and $P2X_7$ sequences. This was taken just C-terminal to the first transmembrane domain from Lys68-Val84 with an N-terminal Cys added for conjugation via a diphtheria toxin domain using maleimidocaproyl-N-hydroxysuccinimide. The epitope for human $P2X_3$ antibody was the equivalent sequence used for rat, while the epitopes for human $P2X_4$ and human $P2X_5$ were Cys270-Asn287 and Cys272-Ser288 respectively. All syntheses were carried out using standard t-BOC chemistry on an ABI synthesiser [43]. The peptide-antigen conjugates were suspended in water at 5 mg/mL and aliquots emulsified by mixing with Complete Freund's Adjuvant. Emulsion volumes of 1 mL containing 2 mg of peptide were injected intramuscularly with second, third, fourth and fifth immunisations followed at 2 week intervals using Incomplete Freund's Adjuvant. Final bleeds via venepuncture were obtained at 10–12 weeks, after it was established that adequate antibody titres had been obtained in the rabbits or sheep used for each epitope. The blood was incubated at 37° C. for 30 min, and stored at 4° C. for 15 h after which the serum was collected following centrifugation and stored at −20° C. in small aliquots. Sera were tested with an ELISA assay for antibodies specific for each peptide [15]. The antibody titre, defined as the reciprocal of the serum dilution resulting in an absorbance of 1.0 above background in the ELISA assay, was in the range 75,000±4,000 compared with 225±25 for the pre-immune samples.

Affinity purification of each of the antibodies against the specific epitope for that antibody resulted in reduced background but identical labelling trends.

EXAMPLE 3

Specificity of Antibodies

Each of the P2X antisera used has been shown to possess similar distributions in many cases but with distinctly different distributions in other cases indicating that the antisera do not lack specificity. Specificity was demonstrated by affinity purification of the sera against the cognate peptides. To further verify antibody specificity, individual antibody such as the antibody to $P2X_1$ was added to cells transfected with the corresponding $P2X_1$ cDNA in the presence and absence of a 10 mM concentration of the $P2X_1$ epitope. Immunolabelling and confocal imaging of the transfected *Xenopus* oocytes demonstrated that the expressed $P2X_1$ is located, as expected, within the cell membrane and the presence of a 10 mM concentration of the cognate peptide as an absorption control resulted in the blocking of $P2X_1$ staining [18].

Individual specificity of all other antibodies has been similarly demonstrated.

EXAMPLE 4

Preparation of Tissue for Ultrastructural Examination of Morphology

Tissue was processed for morphological examination as follows: sections of approximately 3 mm×3 mm in size were fixed in 2.5% glutaraldehyde in 0.1M Tris buffer pH 7.2 for 1 hour. They were then washed and post fixed in 2% aqueous osmium tetroxide for 2 hours. After further washing, the tissue was dehydrated in a graded series of alcohols and embedded in Spurr's resin. Curing was carried out at 50° C. for 18 hours. 100 nm sections were then cut with a diamond knife, stained with uranyl acetate and Reynolds lead citrate in the usual manner and examined in a Phillips 400 transmission electron microscope.

EXAMPLE 5

Ultrastructural Immunocytochemistry

The method of Slater [44] was used. In short, thin sections (100 nm) were cut and retrieved on 300 mesh nickel grids. After incubation in blocking solution (1% BSA in PBS) for 30 min, the sections were placed on the surface of a drop of the blocking solution (with the addition of 0.05% Tween 20) containing HRP-conjugated goat anti-rabbit secondary antibody or HRP-conjugated goat anti-sheep secondary antibody (diluted 1:100) for 1 h at room temperature. Grids were then rinsed three times for 10 min in PBS and placed on drops of goat anti-rabbit secondary antibody conjugated to 10 nm gold (Nanoprobe) for 1 h at room temperature. The grids were then washed twice with PBS followed by one wash with distilled water, for 10 min each and then placed in the vapour of 2% aqueous osmium tetroxide for 1 minute. Sections were then stained with aqueous uranyl acetate solution for 20 min, lead citrate for 10 min, rinsed twice for 10 min in distilled water and examined with a Phillips 400 electron microscope at 80 kV.

EXAMPLE 6

P2X Receptors in Human Cancer Tissue

In a study of 4 normal and 6 human prostate cancer cases, $P2X_1$, $P2X_3$, and $P2X_4$ subtypes were markedly increased in human prostate cancer tissue. There was no labelling at all for these subtypes in normal tissue. The labelling patterns for $P2X_1$ (FIG. 1) in the cancerous tissue were particularly interesting in that there was a greater proportion of labelled acinar epithelial cells with each stage of prostate disease, suggesting a direct correlation between neoplastic transformation and the extent of $P2X_1$ acinar labelling. $P2X_5$ was also increased in some prostate cancer cells (results not shown). There was very little or no labelling for $P2X_5$ in normal tissue.

EXAMPLE 7

Figure 2:
FIG. 2 shows a comparison of prostate epithelium (E) from a young (12 week) rat (left), and tissue from an aged rat (18 months; right). The aged tissue shows marked hyperplasia.

P2X Receptors, Growth, Innervation, and Metabolic Factors, Ionic Calcium Modulation in Young vs Aged Wistar Rats P2X Receptors and Apoptosis Studies comparing prostates from four 12 week-old rats and four 1.5 year-old rats resulted in the detection of a marked increase in epithelial hyperplasia in the aged rats, resembling BPH in humans (FIG. 2). As with the human cancer tissue, $P2X_1$, $P2X_3$, and $P2X_4$ receptors and tyrosine kinase. A receptor antibody were up-regulated in the prostatic epithelium of aged rats, when compared with that of young rats. As previously discussed, this indicates an increase in protein phosphorylation (activation), DNA synthesis, intracellular microtubule expression (organelle transport), up-regulation of adjacent receptors for other neurotransmitters, cell proliferation and an influx of ions (primarily ionic calcium) into the epithelial cells indicating apoptosis. An increase in alpha (1B) (voltage-gated calcium channel), and a reduction in the calcium-regulating hormone stanniocalcin was also observed in the aged rat prostates. PDGF and IGF-I both inhibit apoptosis and were decreased in the aged rats [45]. Thus, the aged rat prostate undergoes apoptosis and similar changes in P2X receptor expression as human prostate cancer tissue, and therefore may be used to investigate prostate cancer aetiology.

Innervation, Other Receptors and metabolic Factors

In the aged rats, there was an increase in microtubular structures in the fibromuscular septa subjacent to the prostatic epithelium. These structures appeared similar in micrographs depicting the apoptosis-associated purinergic receptors $P2X_1$, $P2X_7$, ionic calcium, and the innervation factors VAMP, muscarinic receptor (M2), SV-2, SNAP-25, S100, and transferrin receptor, all of which were up-regulated in the aged rats. Alpha (1B) voltage-gated calcium channels and tyrosine kinase A receptors were also up-regulated in the aged rats. Stanniocalcin was down-regulated while the $P2X_1$ and $P2X_7$ apoptotic calcium channel receptors were up-regulated. These data indicate an increase of calcium ion inflow, metabolic rate, microtubule transport and innervation of the prostatic epithelium in the aged rats, and also suggest that this model could be used to investigate human prostate cancer.

EXAMPLE 8

Breast Cancer Cell Lines

Figure 3:
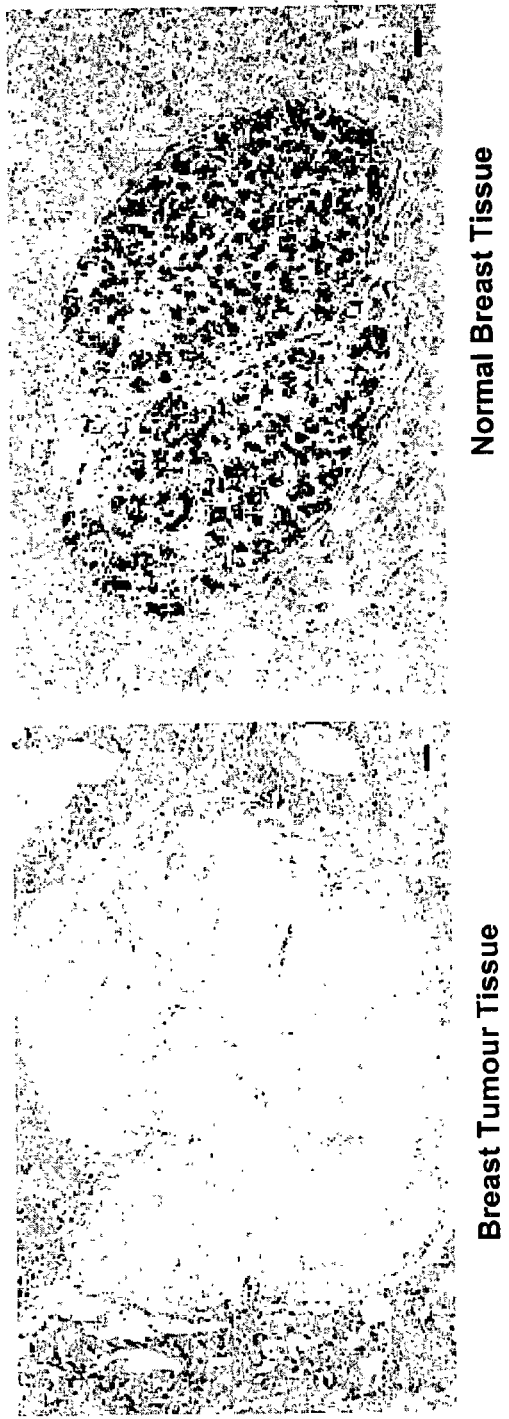
FIG. 3 shows an example of $P2X_1$ labelling in normal breast (right) and of the substantial down-regulation in breast tumour tissue (left).

In 6 breast cancer cell lines supplied as frozen sections, $P2X_1$, $P2X_3$, and $P2X_4$ purinergic subtypes were labelled using the same techniques employed in the labelling of prostate tissues. The labelling pattern (FIG. 3) was suggestive of the labelling patterns seen in both human prostate cancer tissue (FIG. 1) and the prostate of the male aged Wistar rat (FIG. 2).

EXAMPLE 9

Prostate Cancer Diagnoses (FIGS. 4a–f and 5a–f)

The expression characteristics of the purinergic receptor calcium channels ($P2X_{1-7}$) were examined in normal and pathological prostate tissue from 65 cases representing each stage of prostate disease: normal, BPH, preneoplastic and cancerous (Gleason's grade 5–9). Clear translocation features were noted in tissue labelled with $P2X_1$, $P2X_2$, $P2X_3$ and $P2X_7$. After a lengthy process of optimisation and standardisation of P2X antibody production and labelling protocols, a standardised protocol was developed. A mixture of $P2X_1$, $P2X_2$, $P2X_3$ and $P2X_7$ subtypes at a concentration of 0.5 µg/mL IgG each, diluted 1:100 with PBS, proved to be the best reagent for demonstrating the translocation features described. $P2X_4$, $P2X_5$ or $P2X_6$ labelling was of lesser significance. Using this reagent to label tissue sections from each category of prostate cancer it was found that there was a sequential expression and translocation of P2X labelling from the nuclei to the cytoplasm and lateral plasma membranes, ultimately expressing primarily in the apical epithelium, as cancer progressed (FIGS. 4f, 5c, 5f).

Figure 4:
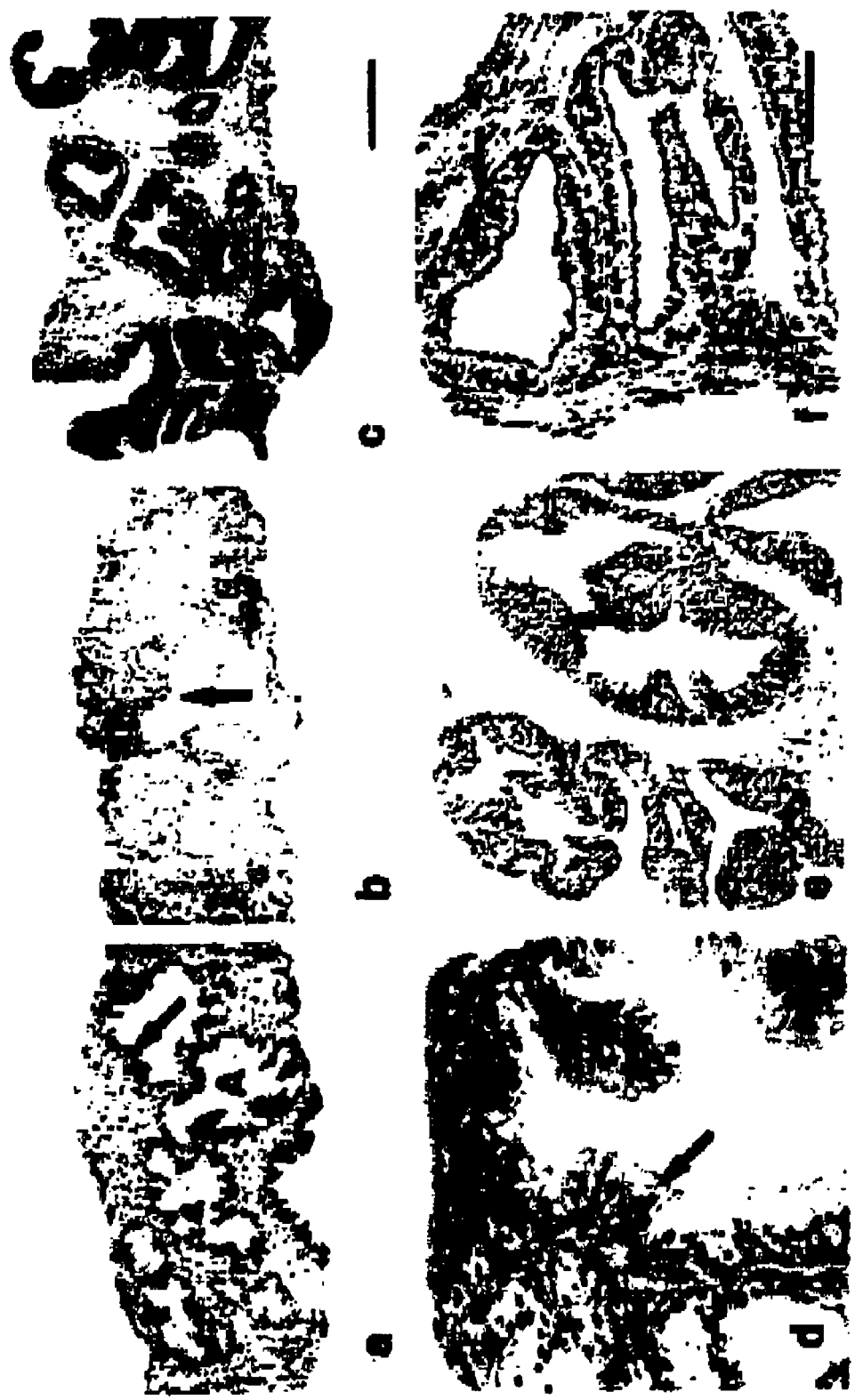
FIGS. 4a, b, d and e show core biopsies from a 71-year old man with increasing PSA. Diagnosis—BPH. The H&E stain (4a) shows mild hyperplasia in the apical epithelium (arrow) of the prostatic acini (A).
FIG. 4d is a high-power micrograph of this area (arrow). Labelling with anti-P2X in the same area (4b) shows the complete de-expression of P2X receptors that is characteristic of BPH (4b-arrow).
FIG. 4e is a high-power micrograph of this area showing complete P2X de-expression in the mildly hyperplasic epithelium (4e-arrow).
FIG. 4c. Section of core biopsy from a 69-year old man. PSA unknown. This case was also diagnosed as BPH by H&E stain (not shown) but features distinctive Stage 1 P2X labelling, as characterised by prominent epithelial nuclei (PEN) (4c-arrow).
FIG. 4f is a high-power micrograph of these densely-labelled nuclei (4f-arrow), as shown in FIG. 4c.
FIGS. 4b, c, e and f, anti-P2X immunoperoxidase label. No counterstain. Bar for low power micrographs (4a, b and c) is 1 cm=150 µm. Bar for high power micrographs (4d, e and f) is 1 cm=40 µm.
Figure 5:
Figure 6:
FIGS. 6a–m show staining patterns in breast cancer biopsy tissue compared with normal tissue.
Figure 6:
Figure 6:
Figure 6:
Figure 6:
Figure 6:
Figure 6:
Figure 6:
Figure 6:
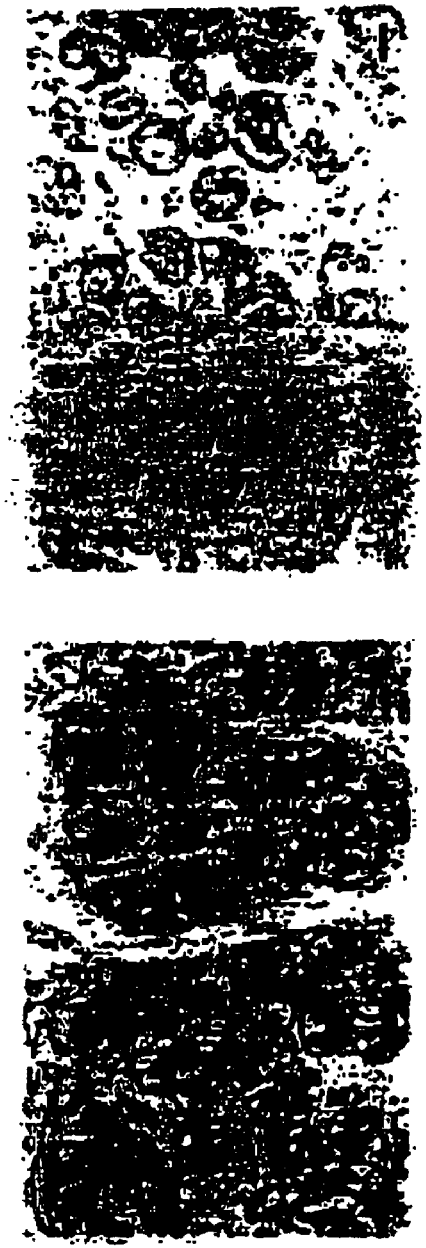
Figure 6:
Figure 6:
Figure 6:

P2X labelling was completely de-expressed in BPH tissue (FIGS. 4b, 4e). Preneoplastic P2X translocation occurred in three distinct stages. Stage 1 was characterised by dense, prominent P2X-labelled epithelial nuclei (PEN) on a pale background (FIGS. 4c, 4f). Stage 2 featured a progressive de-expression of PEN and the appearance of dense and markedly punctate cytoplasmic labelling, nuclear membrane and lateral plasma membrane labelling, and an increasing signal on the apical epithelium (FIGS. 5b, 5c). Stage 3 was represented by nuclei labelled only on the nuclear membrane (NO), no cytoplasmic signal, homogeneous rather than punctate labelling, and a dense label in the apical epithelium (FIGS. 5e, 5f).

In the present study, 56% of cases diagnosed as normal or BPH by haematoxylin and eosin (H&E) staining, showed Stage 1 or Stage 2 P2X labelling. The remaining cases, ranging from Gleason score G5 to G9, had P2X Stage 2 or 3 labelling features. Stage 3 labelling was always accompanied by the histological features of cancer (FIG. 5e). True non-neoplastic BPH tissue was easily distinguished by the complete de-expression of all P2X subtypes in the epithelium and stroma. We propose that biopsy tissue that has been histologically diagnosed as normal but displays P2X labelling features, may be in the process of early (preneoplastic) transformation at a metabolic level. The demonstration of Stage 2 features in 'normal' tissue suggests that the preneoplastic process is more advanced in that tissue. The P2X labelling features described are stage-specific and uniform throughout the entire area of cells representative of each histological classification. In cores that contained both BPH and cancer areas, P2X labelling was clearly and uniformly demarcated into either BPH or one of the cancer labelling patterns. It is proposed that this technique can be used to exclude (and reassure) patients with non-neoplastic prostatic conditions from those with early cancer and also identify rapidly-developing preneoplasia, that may lead to malignancy. This information may permit earlier and more accurate treatment decisions.

EXAMPLE 10

Breast Cancer Diagnoses

Subtypes $P2X_2$, $P2X_3$ and $P2X_7$ are significantly down-regulated in breast cancer biopsy tissue compared with normal. Subtypes $P2X_1$, $P2X_4$, $P2X_5$ and $P2X_6$ were unlabeled in both the normal and cancerous tissue. Tissue was pre-incubated with 3% hydrogen peroxide and 5% horse serum to suppress endogenous peroxidase activity. Examples of the staining patterns are shown in FIGS. 6a–m.

Although the invention has been described with reference to specific examples, it will be appreciated by those skilled in the art that the invention may be embodied in many other forms.

REFERENCES

1. Lian F R, Bhuiyan M, Li Y W, Wall N, Knaut M, and Sarkar F H, 1998 Genistein-Inducted G(2)-M Arrest, P21(Waf1) Upregulation, and Apoptosis in a Non-Small-Cell Lung Cancer Cell Line. Nutr. & Cancer. 31:184–191.
2. Hoey J, 1998 Prostate cancer: progress and perplexity. CMAJ 159:1–3.
3. Kolonel L N, Nomura A M, Hinds M W, Hirohata T, Hankin J H, and Lee J, 1983 Role of diet in cancer incidence in Hawaii. Cancer Res. 43:2397s–2402s.
4. Festuccia C, Vincentini C, di Pasquale A B, Aceto G, Zazzeroni F, Miano L, and Bologna M, 1995 Plasminogen activator activities in short-term tissue cultures of benign prostatic hyperplasia and prostatic carcinoma. Oncol. Res. 7:131–138.
5. Saxena S, Mohanty N K, and Jain A K, 1997 Screening of prostate cancer in males with prostatism. Ind. J. Pathol. Micro. 40:441–450.
6. Diamandis E P and Yu H, 1997 Nonprostatic sources of prostate-specific antigen. Urol. Clin. Nth. Am. 24:275–282.
7. Weyler J, 1999 Prostate cancer: screening or watchful waiting? Ann. Oncol. 9:9–11.
8. Bassler T J, Orozco R, Bassler I C, Odowd G J, and Stamey T A, 1998 Most Prostate Cancers Missed By Raising the Upper Limit of Normal Prostate-Specific Antigen For Men in Their Sixties Are Clinically Significant. Urol. 52:1064–1069.
9. Rabbani F, Stroumbakis N, Kava B R, Cookson M S, and Fair W R, 1998 Incidence and clinical significance of false-negative sextant prostate biopsies. J. Urol. 159: 1247–1250.
10. Gao X, Porter A T, Grignon D J, Pontes J E, and Honn K V, 1997 Diagnostic and prognostic markers for human prostate cancer. Prostate 31:264–281.
11. Small E J, 1997 Prostate cancer. Curr. Opin. Oncol. 9:277–286.
12. Moui J W, Mooneyhan R M, Kao T C, McLeod D G, and Cruess D F, 1998 Preoperative and Operative Factors to Predict Incontinence, Impotence and Stricture After Radical Prostatectomy. Prost. Can. & Prost. Dis. 1:242–249.
13. Drury A and Szent-Gyorgyi A, 1929 The physiological activity of adenine compounds with special reference to their action upon the mammalian heart. J. Physiol. 68:213–237.
14. Abbracchio M and Burnstock G, 1998 Purinergic signalling: pathophysiological roles. Jap. J. Pharmacol. 78:113–145.
15. Hansen M A, Barden J A, Balcar V J, Keay K A, and Bennett M R, 1997 Structural motif and characteristics of the extracellular domain of P2X receptors. Biochem. Biophys. Res. Comm. 236:670–675.
16. Hansen M A, Balcar V J, Barden J A, and Bennett M R, 1998 The distribution of single P2X1-receptor clusters on smooth muscle in relation to nerve varicosities in the rat urinary bladder. J. Neurocytol. 27:529–539.
17. Hansen M, Dutton J, Balcar V, Barden J, and Bennett M, 1999 P2x (purinergic) receptor distributions in rat blood vessels. J. Auton. Nerv. Syst. 75:147–155.
18. Dutton J, Hansen M, Balcar V, Barden J, and Bennett M R, 1998 Development of P2X receptor clusters on smooth muscle cells in relation to nerve varicosities in the rat urinary bladder. J. Neurocytol. in press.
19. Filipovic D M, Adebanjo O A, Zaidi M, and Reeves W B, 1998 Functional and molecular evidence for P2x receptors in Lle-Pkl Cells. Am. J. Physiol. 43:F1070–F1077.
20. Abbracchio M, 1996 P1 and P2 receptors in cell growth and differentiation. Drug. Dev. Res. 39:393–406.
21. Augustine G, Betz H, Bommert K, Charlton M, DeBello W, Hans M, and Swandulla D, Molecular pathways for presynaptic calcium signalling, in Molecular and Cellular Mechanisms of Neurotransmitter Release, L. Stjarne, et al., Editors. 1994, Raven Press: New York, p. 139–155.
22. Di Firgilio F, Pizzo P, Zanovello P, Bronte V, and Collavo D, 1990 Extracellular ATP as a possible mediator of cell-mediated cytotoxicity. Immunol. Today 11:274–277.
23. Siems W, Grune T, Schmidt H, Tikhonov Y, and Pimenov A, 1993 Purine nucleotide levels in host tissues of Ehrlich ascites tumor-bearing mice in different growth phases of the tumor. Cancer Res. 53:5143–5147.
24. Natori Y, Moriguchi M, Fujiwara S, Takeshita I, Fukui M, Iwaki T, and Kanaide H, 1992 Effects of L-NMMA and L-NNA on the selective ATP-induced enhancement of intratumoral blood flow. J. Cereb. Blood Flow Metab. 12:120–127.
25. Figueroa J P and Massmann G A, 1995 Estrogen increases nitric oxide synthase activity in the uterus of nonpregnant sheep. Am. J. Obstet. Gynecol. 173:1539–1545.
26. Rabbani S A and Xing R H, 1998 Role of urokinase (uPA) and its receptor (uPAR) in invasion and metastasis of hormone-dependent malignancies. Int. J. Oncol. 12:911–920.
27. Ciccarelli R, Di Iorio P, Ballerini P, Ambrosini G, Giuliani P, Tibone G, and Caciagli F, 1994 Effects of exogenous ATP and related analogues on the proliferation rate of dissociated primary cultures of rat astrocytes. J. Neurosci. Res. 39:556–566.

28. Potter S W, Gaza G, and Morris J E, 1996 Estradiol induces E-cadherin degradation in mouse uterine epithelium during the estrous cycle and early pregnancy. J. Cell. Physiol. 169:1–14.
29. Kedeshian P, Sternlicht M D, Nguyen M, Shao Z M, and Barsky S H, 1998 Humatrix, a Novel Myoepithelial Material Gel With Unique Biochemical and Biological Properties. Cancer Lett. 123:215–226.
30. Dethlefsen S M, Raab G, Moses M A, Adam R M, Klagsbrun M, and Freeman M R, 1998 Extracellular calcium influx stimulates metalloproteinase cleavage and secretion of heparin-binding EGF-like growth factor independently of protein kinase C, J. Cell. Biochem. 69:143–153.
31. Barclay A, 1981 The localisation of populations of lymphocytes defined by monoclonal antibodies in rat lymphoid tissues. Immunology 42:593–600.
32. Valera S, Hussy N, Evans R J, Adami N, North R A, Surprenant A, and Buell G, 1994 A new class of ligand-gated ion channel defined by P2x receptor for extracellular ATP [see comments]. Nature 371:516–519.
33. Brake A J, Wagenbach M J, and Julius D, 1994 New structural motif for ligand-gated ion channels defined by an ionotropic ATP receptor. Nature 371:519–523.
34. Lewis C, Neidhart S, Holy C, North R A, Buell G, and Surprenant A, 1995 Coexpression of P2X2 and P2X3 receptor subunits can account for ATP-gated currents in sensory neurons [see comments]. Nature 377:432–435.
35. Buell G, Collo G, and Rassendren F, 1996 P2X receptors: an emerging channel family. Eur. J. Neurosci. 8:2221–2228.
36. Collo G, North R A, Kawashima E, Merlo-Pich E, Neidhart S, Surprenant A, and Buell G, 1996 Cloning OF P2X5 and P2X6 receptors and the distribution and properties of an extended family of ATP-gated ion channels. J. Neurosci. 16:2495–2507.
37. Surprenant A, Rassendren F, Kawashima E, North R A, and Buell G S, 735–738., 1996 The cytolytic P2Z receptor for extracellular ATP identified as a P2X receptor (P2X7). Science 272:735–738.
38. Rassendren F, Buell G N, Virginio C, Collo G, North R A, and Surprenant A, 1997 The permeabilizing ATP receptor, P2X7. Cloning and expression of a human cDNA. J. Biol. Chem. 272:5482–5486.
39. Longhurst P A, Schwegel T, Folander K, and Swanson R, 1996 The human P2x1 receptor: molecular cloning, tissue distribution, and localization to chromosome 17. Biochim. Biophys. Acta 1308:185–188.
40. Garcia-Guzman M, Stuhmer W and Soto F, 1997 Molecular characterization and pharmacological properties of the human P2X3 purinoceptor Brain Res. Mol. Brain Res. 47, 59–66.
41. Garcia-Guzman M, Soto F, Gomez-Hernandez J M, Lund P E, and Stuhmer W, 1997 Characterization of recombinant human P2X4 receptor reveals pharmacological differences to the rat homologue. Mol. Pharmacol. 51, 109–118.
42. Le K T, Paquet M, Nouel D, Babinski K and Seguela P, 1997 Primary structure and expression of a naturally truncated human P2X ATP receptor subunit from brain and immune system FEBS Lett. 418, 195–199.
43. Barden J A, Cuthbertson R M, Jia-Zhen W, Moseley J M, and Kemp B E, 1997 Solution structure of parathyroid hormone related protein (residues 1–34) containing an Ala substituted for an Ile in position 15 (PTHrP[Ala15]-(1–34)). J. Biol. Chem. 272:29572–29578.
44. Slater M, Patava J, Kingham K, and Mason R S, 1994 Modulation of growth factor incorporation into the extracellular matrix of human osteoblast-like cells in vitro by 17β estradiol. Am. J. Physiol. 267:E990–E1001.
45. Kiess W and Gallaher B, 1998 Hormonal control of programmed cell death/apoptosis. Eur. J. Endocrinol. 138: 482–491.

The invention claimed is:

1. A method of diagnosing prostate cancer in a subject, comprising detecting the expression profile of $P2X_1$, $P2X_2$, $P2X_3$, and/or $P2X_7$ purinergic receptors in prostate cells and/or tissue from the subject using $P2X_1$, $P2X_2$, $P2X_3$ and/or $P2X_7$ antibody respectively, wherein an increase in the intensity of the P2X purinergic receptor expression profile in the prostate cells and/or tissue, compared to the expression profile of prostate cells and/or tissue from a prostate having benign prostate hyperplasia, is diagnostic of the presence of prostate cancer.

2. A method of diagnosing breast cancer in a subject comprising detecting the expression profile of $P2X_2$, $P2X_3$, and/or $P2X_7$ purinergic receptors in breast cells and/or tissue from the subject using $P2X_2$, $P2X_3$, and/or $P2X_7$ antibody respectively, wherein a decrease in the intensity of the P2X purinergic receptor expression profile in the breast cells and/or tissue compared to the expression profile of breast cells and/or tissue from the breast of a normal subject, is diagnostic of the presence of breast cancer.

3. A method according to any one of claims 1 or 2 wherein the antibody reagent comprises a polyclonal antiserum.

4. A method according to any one of claims 1 or 2 wherein the antibody reagent comprises a monoclonal antibody.

* * * * *